United States Patent
Diamond et al.

(10) Patent No.: US 6,395,233 B1
(45) Date of Patent: May 28, 2002

(54) RAPID DIALYSIS CELL AND METHOD FOR AUTOMATED INSTRUMENTATION

(75) Inventors: Ronald N. Diamond, Anaheim Hills; William A. Stark, Costa Mesa, both of CA (US)

(73) Assignee: Quest Diagnostics Investments, Inc., Wilmington, DE (US)

( * ) Notice: Subject to any disclaimer, the term of this patent is extended or adjusted under 35 U.S.C. 154(b) by 0 days.

(21) Appl. No.: 09/476,187

(22) Filed: Jan. 3, 2000

(51) Int. Cl.⁷ .......................... B01D 63/00; B01D 63/05
(52) U.S. Cl. ...................... 422/101; 210/474; 210/454; 210/321.84; 210/321.78
(58) Field of Search ................................ 210/644, 473, 210/477, 482, 474, 321.84, 416.1, 321.78, 767, 454; 422/101, 100; 600/569

(56) References Cited

U.S. PATENT DOCUMENTS

| 4,145,293 A | * | 3/1979 | Cook |
| 4,879,030 A | * | 11/1989 | Stache |
| 4,963,256 A | | 10/1990 | Nelson |
| 4,983,282 A | * | 1/1991 | Roy et al. |
| 5,015,398 A | * | 5/1991 | Cocuzzi |
| 5,032,268 A | * | 7/1991 | Hahn |
| 5,079,170 A | * | 1/1992 | Rosman et al. |
| 5,609,760 A | * | 3/1997 | Leach |
| 5,658,463 A | * | 8/1997 | Rubio |
| 5,996,423 A | * | 12/1999 | Baghel et al. |
| 6,063,038 A | * | 3/2000 | Diamond et al. |

* cited by examiner

Primary Examiner—Ana Fortuna
(74) Attorney, Agent, or Firm—Stout, Uxa, Buyan & Mullins, LLP; Donald E. Stout; Greg S. Hollrigel

(57) ABSTRACT

An improved dialysis cell and method for using the same to achieve shorter dialysis times wherein the two dialysis solutions used in the dialysis are brought into greater mutual contact with a semipermeable membrane, requiring the use of a smaller volume of dialysis. Because the dialysis cell is substantially rigid and in the shape of a test tube it can be used with an automated pipettor.

29 Claims, 5 Drawing Sheets

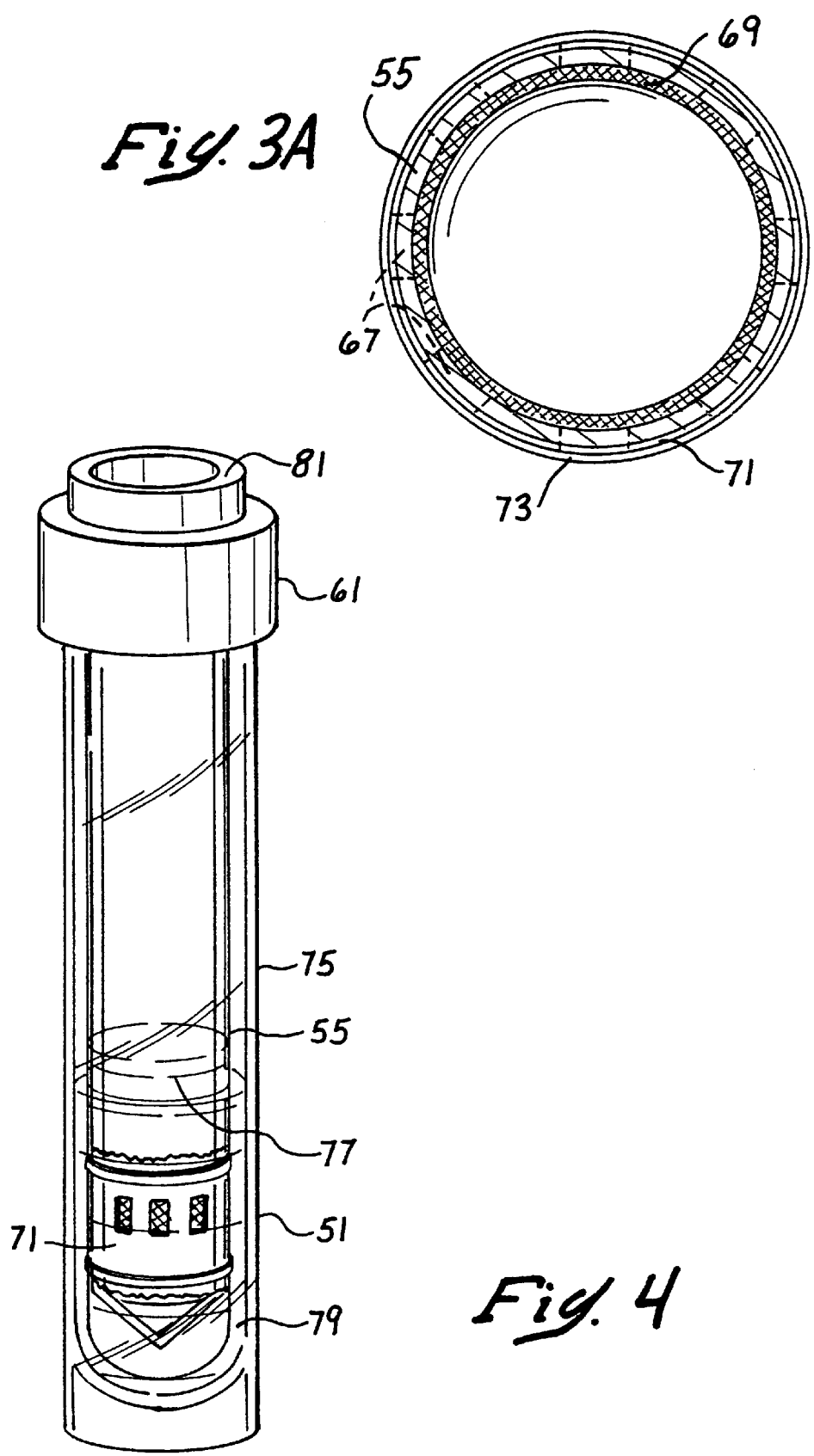

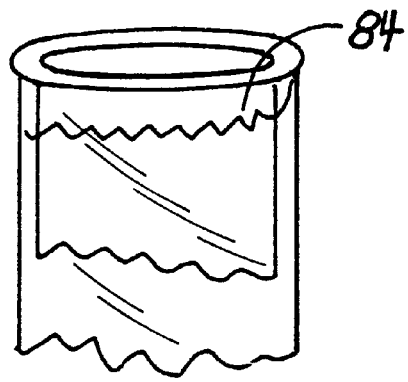
Fig. 5A
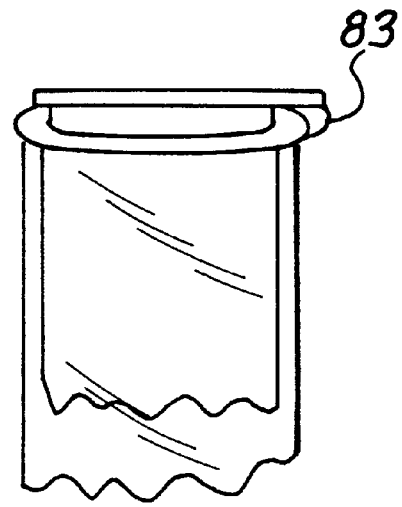
Fig. 5B'
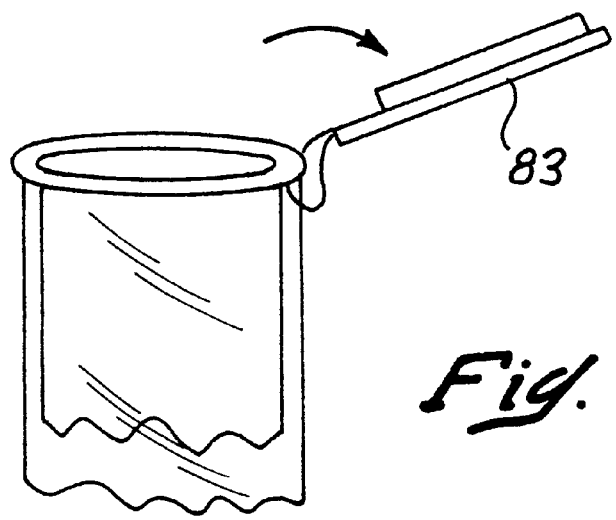
Fig. 5B"

RAPID DIALYSIS CELL AND METHOD FOR AUTOMATED INSTRUMENTATION

BACKGROUND OF THE INVENTION

The present invention relates to the field of methods and devices for preparing samples for chemical analysis. This invention relates more particularly to equilibrium dialysis cells and a dialysis of a unique configuration and efficiency for assaying biological samples, as well as assaying biological samples with an automated pipettor.

There are many existing assays that measure the concentration of a desired molecule or ion in solution, referred to herein to as an analyte. For example a user might want to test for the concentration of the analytes thyroxine, estradiol or testosterone in a blood sample.

There are a wide variety of chemical analytic techniques used to detect analyte, such as chromatography, chemoluminesce, radioimmunoassay (RIA), Enzyme Immunoassay, Enzyme-Linked-ImmunoSorbent-Assay (ELISA) and flow techniques. These tests typically attach a marker to the analyte and then test for the presence of the marker to determine the presence of the analyte itself.

It is difficult however to measure analyte directly from a raw sample because in many instances the analyte is found in the sample as a solution of both free analyte and bound analyte. Bound analyte is usually bound to a high-molecular weight protein, and is a type of interference. An interference will react to the assay in the same manner as will the free analyte. More generally an interference is a substance, other than the material desired to be assayed, that also responds to the chosen analytical method thereby distorting the results, or a material that can prevent the assayed material from being measured at all.

In addition to the bound analyte there are other interferences commonly found in a raw sample. The sample may contain impurities such as larger molecules or solid components which can lead to adulterated analysis results. Impurities which commonly occur in sampling are, for example, extraneous proteins found when analyzing food; filter fibers and dust particles are commonly a problem when analyzing environmental samples.

When samples of assays contain interferences the results must be arrived at by analog means. For example, when there is bound analyte acting as an interference, analog means are arrived at by correlating the apparent result with standardized models to calculate an approximation of free analyte found in a given sample. The amount of free analyte present in the solution is estimated based on a characteristic ratio of bound analyte to free analyte found in past tests using the same technique for the same analyte.

Analog testing is essentially guesswork and at best is only an estimate of the free analyte. Analog determination is further complicated and unreliable because the ratio of free analyte to bound analyte may vary depending on the disease state of the patient, medications the patient is taking, etc.

Interferences can first be separated from the raw sample to produce a more accurate direct measurement. Equilibrium dialysis can be used for purifying a raw sample to extract the analyte to be assayed. The purified free analyte is separated from the bound analyte and other impurities and then measured alone. A dialysis cell and method of analyte separation is the subject of the present invention.

A problem with the use of equilibrium dialysis is the relatively long time it takes for the dialysis reaction to take place.

Dialysis is the separation of suspended colloidal particles in solution, the retentate, from the dissolved analyte ions or molecules of small dimensions. This separation is achieved by taking advantage of their unequal rates of diffusion through the pores of a semipermeable membrane. Equilibrium dialysis takes place across a semipermeable membrane by action of osmotic pressure. A semipermeable membrane is placed between a raw sample held in one chamber and an acceptor solution, the dialysate, held in a second chamber. The dialysate is a dialysis buffer solution that is chemically compatible with a given retentate and analyte. These two chambers together with the semipermeable membrane comprise a basic dialysis cell.

The permeability of the membrane is designed such that the analytes can migrate through the semipermeable membrane but the retentate and other interferences are excluded from migrating through to the dialysate. The retentate and other interferences are typically of a larger molecular weight and the semipermeable membrane allows only those molecules of lower molecular weight to migrate. The size or weight at which the largest molecule can migrate through a given semipermeable membrane is termed the Molecular Cut-Off Weight (MWCO).

Separation by dialysis is a slow process, the rate of dialysis depending in part on the differences in particle size and diffusion rates between the analyte and the non-analyte constituents. The rate at which the dialysis occurs depends on several other factors, some of which are the ratio of the analyte molecular weight to the membrane MWCO, the surface area of the membrane mutually contacted by the sample and the dialysate, the temperature of the two solutions and the amount of diffusion of substances that must first occur within both solutions for total equilibrium to be reached.

The diffusion that must take place in order for the dialysis to proceed to final equilibrium is slowed when the ratio of the membrane surface area that contacts either the retentate or the dialysate is small compared to the volume of its respective chamber. The reaction may also be impeded by molecules of the retentate and other interferences blocking the pores of the semipermeable membrane.

The analytes migrate through the membrane into the acceptor dialysate solution until an equal concentration on both sides of the membrane is established. As the dialysis process occurs, concentration gradients on either side of the membrane limit the rate of migration of analyte. The net migration of the analyte is directed toward the dialysate chamber and takes place as long as the concentration of the analytes in the sample chamber is larger than in the dialysate. At equilibrium the concentration of the analytes in the dialysate comprises a value identical to that of the retentate sample.

Current methods and devices used for dialysis require very long dialysis times to reach equilibrium, in some instances 17 hours or more.

One type of dialysis cell utilizes reusable blocks with injection ports in the sides to inject the sample or the dialysate. Membranes are placed between the blocks and dialysate and sample are alternately injected into the reusable blocks through the ports. A series of blocks may be sandwiched together in an alternating block/membrane/block fashion.

As used herein a first dialysis solution means either the sample or the dialysate. A second dialysis solution means the sample or dialysate as well, but the one of these two solutions not selected as the first dialysis solution.

The dialysis cell of the Nelson U.S. Pat. No. 4,963,256 utilizes an outer chamber containing a first dialysis solution. There is also provided an inner chamber which containing a second dialysis solution. The end of the inner cylindrical chamber is covered by a semipermeable membrane and inserted within the outer container. Because the semipermeable membrane of the Nelson cell covers only the end of a cylindrical member however, only about 90 mm$^2$ of surface area of semipermeable membrane is available to mutually contact both of the dialysis solutions for dialysis.

In addition to the great amount of time it takes to allow both liquids to equilibrate, existing dialysis cells generally cannot be readily used with automated laboratory equipment such as an automatic pipettor. In most cases a dialysis cell must be individually loaded with the sample and the dialysate solution, requiring time and expensive manual labor to accomplish.

What is needed then is a dialysis cell that can take advantage of one or more of the variables in dialysis cell design to reduce the time that it takes for dialysis to reach equilibrium. What is also needed is a method to use a dialysis cell to shorten equilibrium time.

What is also needed is a dialysis cell that can be used with automated pipetting equipment to both increase the number of dialysis assays that can be done as well as to reduce the expense of manual labor to perform these tests.

It is therefore a first object of the present invention to provide a dialysis cell of a design that affords the maximum available semipermeable membrane surface area in mutual contact with both the analyte and the dialysate solution.

A second object of this invention is to minimize the time of reaching equilibrium in a dialysis cell by maximizing the surface area of the semipermeable membrane relative to the volume of the solutions used to perform the dialysis, thereby reducing the time needed for diffusion of the solutions during dialysis.

A third object of this invention is to provide a dialysis cell and method for its use that will allow using the dialysis cell with an automated pipettor.

SUMMARY OF THE INVENTION

The dialysis cell of the present invention encompasses a substantially rigid elongate outer container in the general shape of a test tube, the outer container having an open end and a closed end. There is also provided a substantially rigid elongate inner container, also having an open end and a closed end and sized to fit inside of the outer container and conform closely to the shape of the outer container.

The inner container centrally displaces liquid placed in the outer container when it is inserted therein, causing the liquid to envelope in the inner container. The space comprising the volume of the inner container is centrally displaced by a displacing member, which is comprised of either the design of the inner container itself, for example a portion of the closed end of the inner container being centrally inverted into the inner container, or, for example, is comprised of a second member placed in the inner container, such as a plunger to centrally displace the liquid of the inner container. This central displacement of the liquid in the inner container causes the liquid in the inner container to come into greater contact with the inner wall of the inner container and therefore also a semipermeable membrane contoured on or around the inner wall of the inner container.

The lengthwise portion of the elongate inner container wall incorporates a semipermeable membrane through which dialysis takes place. When the liquids of both the outer container and the inner container are centrally displaced they are brought into greater mutual contact with the semipermeable membrane.

In the preferred embodiment the incorporated semipermeable membrane is provided by one or more fluid permeable apertures in a portion of the lengthwise wall of the inner container. The apertures are covered with semipermeable membrane. the fluid permeable apertures in a portion of the lengthwise wall of the inner container are first covered with porous mesh for structural support of the semipermeable membrane, the semipermeable membrane is applied over the porous mesh.

The invention takes advantage of the additional membrane surface area that may be utilized by placing semipermeable membrane along the length of the inner container. The closed end of the inner container may be additionally provided with apertures and semipermeable membrane for creating additional available surface area. This design provides more available membrane surface area while maintaining the advantages of having a substantially rigid tube that may be used in an automated pipettor machine. The automated pipettor machine may be used to move the dialysis cell, to introduce a dialysis solution to the inner container or the outer container, or to remove a dialysis solution from the inner container or outer container.

A first dialysis solution is placed in the outer container, the serum retentate sample is used in the preferred embodiment, then the inner container is inserted into the outer container. A second dialysis solution is placed within the inner container, the dialysate in the preferred embodiment, creating a dialysis cell. The two containers are attached to each other to hold them in fixed relation.

The open end of the inner container and the open end of the outer container are designed to be threadably attached after the inner container is inserted into the outer container, holding the two containers in fixed relation to each other. Alternatively for example, the inner container may be inserted into the outer container and a threaded cap affixed to the outer container, holding the inner container in. The inner container and the outer container may be attached in any convenient way, for another example by attaching the open ends of the two containers with a snap-lock to each other, with complementary snap-lock flanges on the open end of each container. These designs are well known in the art and are presented by way of example and are not exhaustive of the alternative ways to attach the open ends of the two containers.

In a first embodiment of the dialysis cell the closed end of the inner container is concave and centrally inverted into the inner container in order to centrally displace the solution within the inner container and cause the available solution to come into greater contact with the surface area of the wall of the inner container incorporating the semipermeable membrane. Centrally displacing the solution in this manner reduces the volume of solution needed to inundate the available semipermeable membrane and the decrease in volume also decreases the time needed for any intra-solution diffusion to take place.

A portion of the wall running along the length of the inner container, excluding the inverted portion, has apertures to allow fluid communication between the inner container and the outer container. The apertures of the inner wall of inner container are first covered with porous mesh to provide support for semipermeable membrane, then a semipermeable membrane is placed over the apertures on the outer wall of the inner container. Use of the porous mesh is of course not necessary if a given semipermeable membrane does not require the additional structural support of the porous mesh because the apertures are small enough or the membrane is strong enough in such properties as tensile and shear strength to cover the apertures by itself without tearing. The porous mesh may also be placed on the outside wall of the inner container over the apertures, then the semipermeable membrane placed thereover.

The outer container is supplied with a first dialysis solution, then the inner container is supplied with a second dialysis solution and placed in the outer container. The outer container and the inner container are attached at their respective open ends, holding the two containers tightly with respect to one another. In this embodiment the inner container may also have a thin puncturable film covering the open ends of both containers.

The dialysis reaction is then allowed to proceed to equilibrium. A quantity of the dialysate is taken after equilibrium and subjected to one of the above-recited analyses to determine serum concentration of the analyte.

In a second embodiment an elongate outer container is provided, having an open end and a closed end. There is also provided an inner container that closely conforms to the outer container, the inner container having an open end and a closed end. A wall portion of the inner container between the open end and the closed end has apertures to allow fluid communication between the inner container and the outer container.

In the preferred embodiment the inner wall of the inner container having apertures is covered with porous mesh to provide support for a semipermeable membrane, then a semipermeable membrane is secured over the apertures on the outer wall of the inner container. The outer container is then supplied with a first dialysis solution. The inner container is supplied with a second dialysis solution and placed in the outer container, creating a dialysis cell. The outer container and the inner container are attached holding the two tubes in fixed relation to each other.

A plunger is then inserted into the inner container to drive the dialysis solution of the inner container up the length of the interior of the inner container. The porous mesh acts to guide the plunger to be centrally located within the inner container, maintaining a uniform distance of about 250 μm between the plunger and the interior wall of the inner container. This configuration results in a shorter equilibrium dialysis time because there is both a greater area of semipermeable membrane in mutual contact with both dialysis solutions and the time necessary for diffusion is greatly reduced because there is a smaller volume of ambient dialysis solution within which any diffusion of an analyte has to take place.

In the above manner dialysis time can be substantially reduced from the current average of, for example, seventeen hours. The new design also allows freedom from human intervention because the dialysis cells can be prepared in advance with dialysate buffer solution placed within the outer container. The user simply adds the sample to the inner container and allows the dialysis to go to equilibrium. After reaching equilibrium the user removes the inner container and inserts a probe into the prepared tube of dialysate.

Alternatively, the inner container may be prepared in advance by being filled with dialysate. The user then adds the sample to the outer container and inserts the inner container.

These new designs can also be used with automated equipment because they are in the general shape of a test tube and require only the insertion of a quantity of sample into one of the containers.

Additional aspects and advantages of the present invention are set forth in the following description and claims, particularly when considered in conjunction with the accompanying drawings in which like parts bear like reference numerals.

BRIEF DESCRIPTION OF THE DRAWINGS:

FIG. 1A is a cross sectional view of the inner container of FIG. 1.

FIG. 3A is a cross sectional view of the inner container of FIG. 3.

FIG. 4 is a schematic view of the assembled components of the second embodiment of the present invention.

FIG. 5A is a partial schematic view of the second embodiment of the present invention detailing the use of a thin film to cover the assembled invention.

FIG. 5B' is a partial schematic view of the second embodiment of the present invention detailing the use of a snap-lock lid in the closed position to cover the assembled invention.

FIG. 5B" is a partial schematic view of the second embodiment of the present invention detailing the use of a snap-lock lid in the open position to cover the assembled invention.

DETAILED DESCRIPTION OF THE INVENTION

Figure 1:
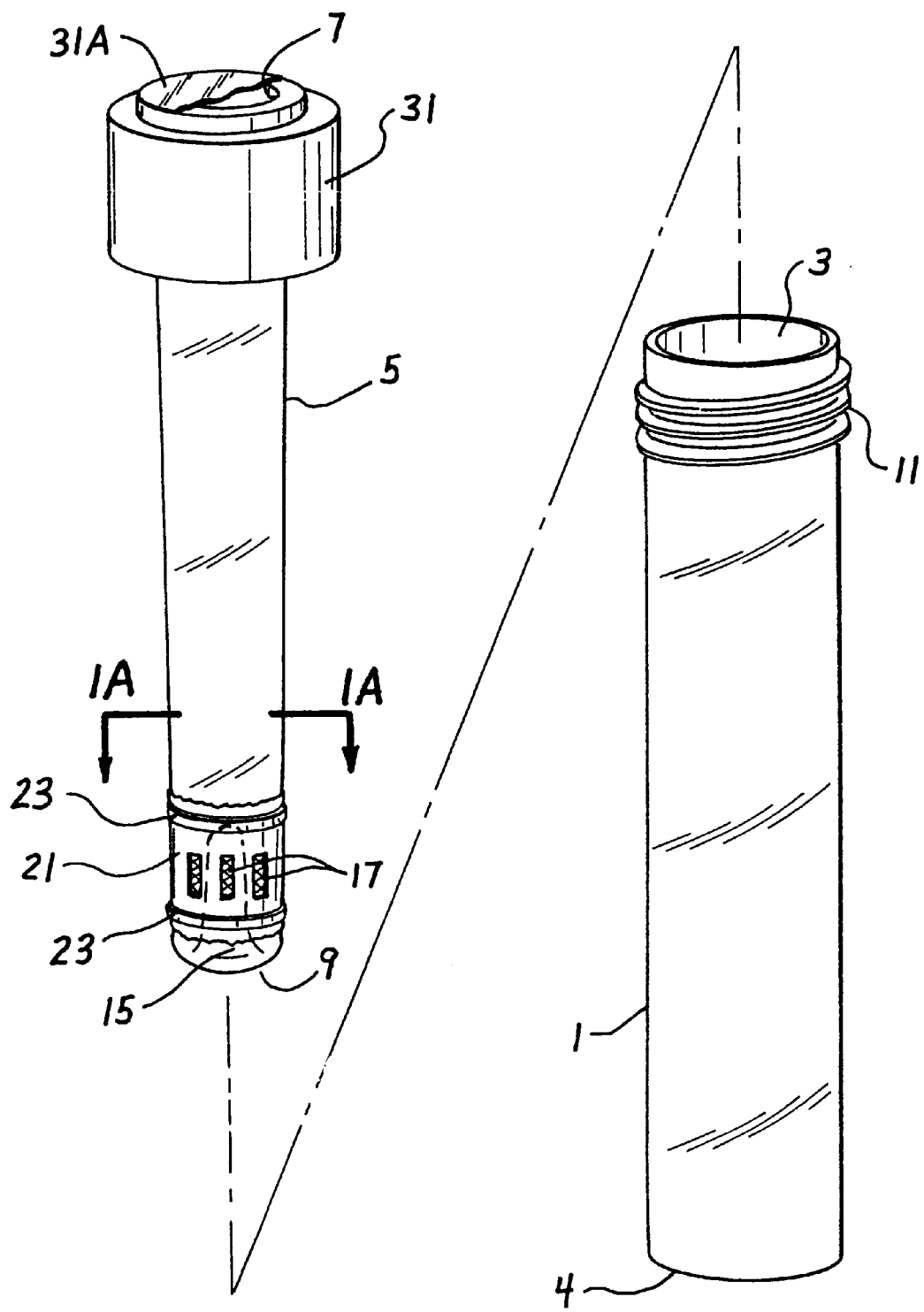
FIG. 1 is a schematic view of the components of the first embodiment of the present invention.

Referring now to FIG. 1 there is shown the components of a first embodiment of the dialysis cell of the present invention. There is provided an elongate outer container 1 in the general shape of a test tube having an open end 3 and a closed end 4. The inventors contemplate for most applications the outer container will have dimensions of approximately 16 mm in diameter and 79 mm in length and be made of a substantially rigid clear polypropylene, acrylic, or other suitable material. The outer container of this and any embodiment must be rigid enough to allow use of the dialysis cell with an automated pipettor, which will hold and insert the dialysis cell into a dialysis cell holder much alike to a test tube rack. Inner container 5 conforms closely to the outer container, the inner container also having an open end 7 and a closed end 9.

The open end of the outer container 3 and the open end of the inner container 7 are formed to be capped by a cap 31 that is formed as a flange extending from open end 7 and a skirt extending downwardly therefrom, having internal threads (not shown). The central portion of the cap in the embodiment depicted is made of a thin film 31A, to allow for example a pipette needle to be used to puncture the thin film to fill the inner container.

In this embodiment the closed end of the inner container is concave and centrally inverted into the inner container, forming an inverted portion 15. The wall of the inner container along the length of the wall next to the inverted portion has apertures 17 to allow fluid communication between the inner container and the outer container after the inner container has been inserted in the outer container.

FIG. 1A is a cross-sectional view shown along the A—A sectional line of the inner container of FIG. 1, and shows the inner wall of the inner container. The apertures 17 of the inner container are covered with porous mesh 19 on the inner wall of the inner container, around inverted section 15. The apertures are covered with semipermeable membrane 21 on the outer wall of the inner container and held fast with O-rings 23.

Referring again to FIG. 1, the porous mesh provides support for a semipermeable membrane 21 that is placed over the outer wall of the inner container over the apertures. Use of the porous mesh is of course not necessary if a given semipermeable membrane does not require the additional structural support of the porous mesh because the apertures are small enough or the membrane is strong enough in such properties as tensile and shear strength to cover the apertures by itself without tearing during dialysis. The semipermeable membrane is held fast over the outer wall of the inner container by O-rings 23 at either end of the semipermeable membrane. The semipermeable membrane is of the type well known in the art and in this embodiment would be approximately 0.05 mm thick and 18 mm long.

Figure 2:
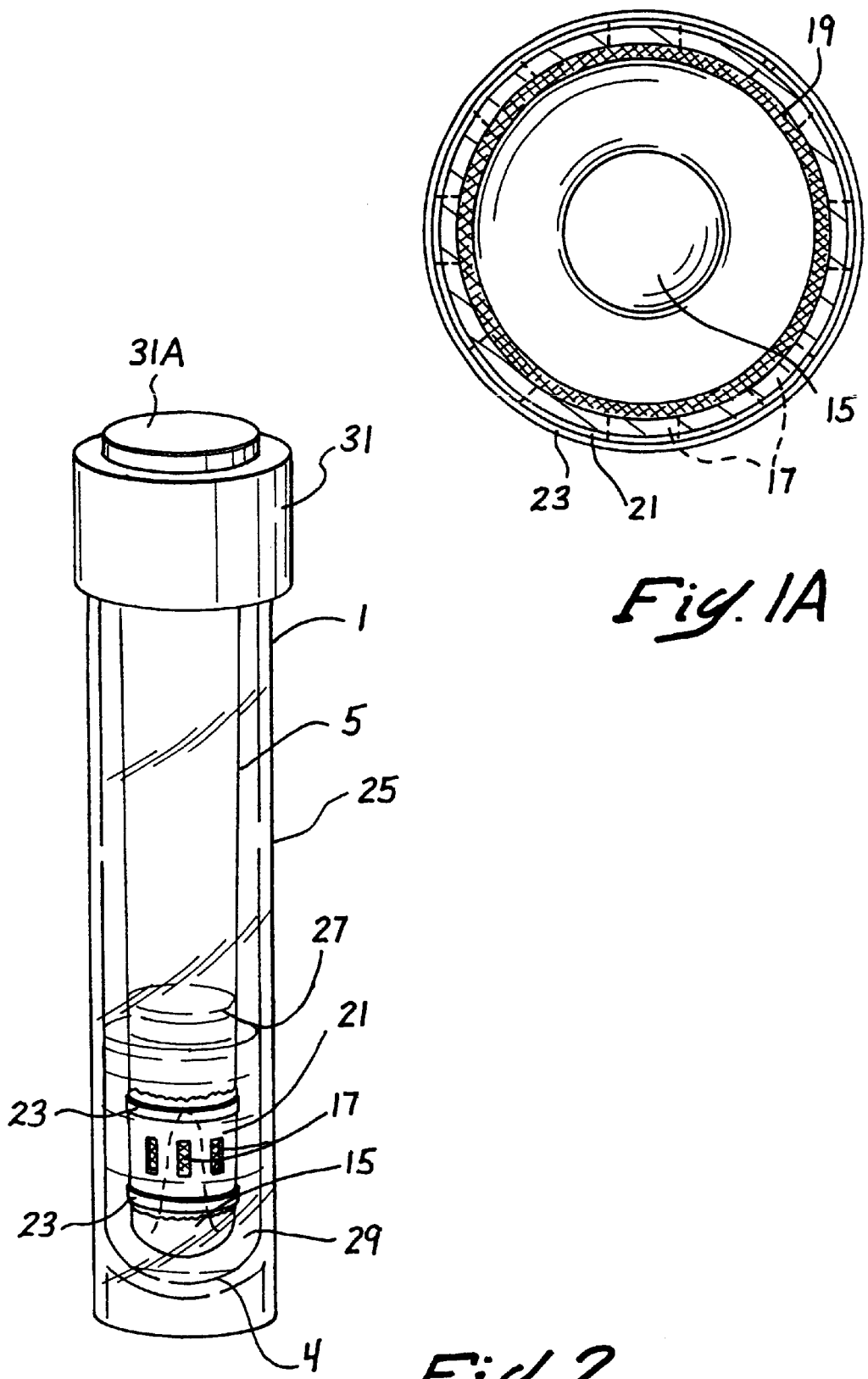
FIG. 2 is a schematic view of the assembled components of the first embodiment of the present invention.

Referring now to FIG. 2, an assembled dialysis cell 25 of the first embodiment is shown. Elongate inner container 5 has been placed within elongate outer container 1 and cap 31 has been screwed on to cover threads 11 (shown in FIG. 1). A first dialysis solution, shown at 27, placed in the inner container is centrally displaced around the inverted portion 15 sufficient to cause the first dialysis solution to rise to a level above the semipermeable membrane 21. The inverted portion thereby allows less dialysis solution to be used than would be otherwise needed to cover the apertures and semipermeable membrane.

A second dialysis solution 29 is in the outer container and is centrally displaced around the inner container sufficient to cover the semipermeable membrane 21. The inner container centrally displaces the second dialysis solution and thereby allows less dialysis solution to be used than would be otherwise needed to cover the semipermeable membrane.

Figure 3:
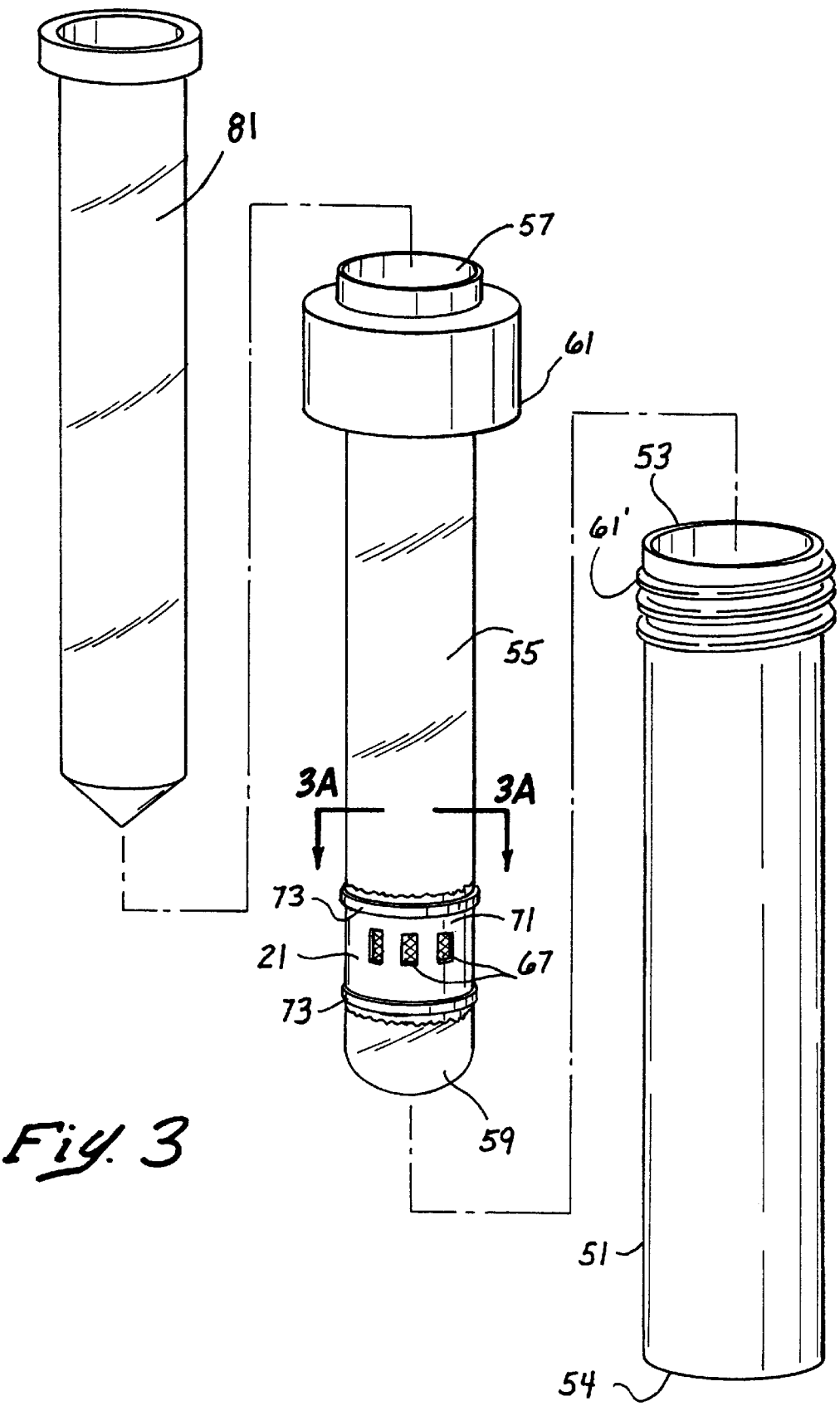
FIG. 3 is a schematic view of the components of the second embodiment of the present invention.

Referring now to FIG. 3 there is shown the components of a second embodiment of the dialysis cell of the present invention. There is provided an elongate outer container 51 in the general shape of a test tube having an open end 53 and a closed end 54. The inventors contemplate for most applications the outer container will have dimensions of approximately 16 mm in diameter and 79 mm in length and be made of a substantially rigid clear polypropylene, acrylic, or other suitable material. The outer container of this and any embodiment must be rigid enough to allow use of the dialysis cell with an automated pipettor, which will hold and insert the dialysis cell into a dialysis cell holder much like a test tube rack. Inner container 55 conforms closely to the outer container, the inner container also having an open end 57 and a closed end 59.

The open end of the outer container 53 and the open end of the inner container 57 are formed to be threadably attached, with the inner container forming the external overlying threads on a flange having a skirt 61 that is disposed about the open end of the outer container and is formed to be threadably joined to outer container threads 61'.

The wall of the inner container has apertures 67 to allow fluid communication between the inner container and the outer container after the inner container has been inserted in the outer container.

FIG. 3A is a cross-sectional view shown along the A—A sectional line of the inner container 55 of FIG. 3, and shows the inside wall of the inner container. The apertures 67 of the inner container are covered with porous mesh 69 on the inner wall of the inner container. The apertures are covered with semipermeable membrane 71 on the outer wall of the inner container and held fast with O-rings 73.

Referring again to FIG. 3, the porous mesh provides support for a semipermeable membrane 71 that is placed over the outer wall of the inner container over the apertures. Use of the porous mesh is not necessary if a given semipermeable membrane does not require the additional structural support of the porous mesh because the apertures are small enough or the membrane is strong enough in such properties such as tensile strength and shear strength to cover the apertures by itself without tearing during dialysis. The semipermeable membrane is held fast over the outer wall of the inner container by O-rings 73 at either end of the semipermeable membrane. The semipermeable membrane is of the type well known in the art and in this embodiment would be approximately 0.05 mm thick and 18 mm long.

Referring now to FIG. 4, the assembled dialysis cell 75 of the second embodiment is shown. Elongate inner container 55 has been placed within elongate outer container 51 and the threads of the two containers have been screwed together at flange 61. A plunger 81 is inserted within the inner container 55 as indicated by the arrow. The shape of the tip of the plunger should best conform to the shape of the inner wall of the closed end, noting that a rounded tip should be used where the closed end itself incorporates semipermeable membrane. A first dialysis solution, shown at 77, in the inner container is centrally displaced around the plunger 81 sufficient to cause the first dialysis solution to rise to a level above the semipermeable membrane 71. The plunger thereby allows less dialysis solution to be used than would otherwise be needed to cover the apertures and semipermeable membrane.

A second dialysis solution 79 is in the outer container and is centrally displaced around the inner container sufficient to cover the semipermeable membrane 71. The plunger in the inner container centrally displaces the second dialysis solution and thereby allows less dialysis solution to be used than would be otherwise needed to cover the semipermeable membrane.

Referring now to FIGS. 5A, 5B' and 5B", there are shown as examples the coverings that may alternatively be used with one or more embodiments of the invention, these examples are not meant to be limiting. In FIG. 5A the open ends of the containers are commonly covered by a heat-sealed thin puncturable film shown at 84. FIGS. 5B' and 5B" depict the open ends of the containers being commonly covered by a snap-lock lid 83, FIG. 5B' shows the lid in the closed position and FIG. 5B" shows the lid in the open position.

EXEMPLARY USE

The following is an exemplary use of the invention.

In the present context there are two dialysis solutions used in a dialysis cell, the sample solution and the dialysate buffer solution. Either one may be used as a first dialysis solution and the remaining solution is denominated herein as the second dialysis solution, for purposes of this description. In the first embodiment the outer container is first supplied with about 2.4 ml of a first dialysis solution and the inner container is then placed into and affixed to the outer container. In this embodiment the outer container and the inner container are attached by use of a cap, shown in FIG. 2 at 31, holding the two tubes tightly with respect to one another and maintaining a uniform distance of less than 1 mm between the inner container and the inner container.

About 0.2 ml of the second dialysate solution is then introduced into the inner container either by puncturing the thin puncturable film of the open end of the inner container or by opening the snap-lock cap, depending on which type of covering is used with the dialysis cell. The dialysis cell is then placed in an incubator and the reaction allowed to proceed to equilibrium. The dialysis cell is placed in an incubator because the dialysis reaction is best carried out at an ambient temperature of 37 degrees Celsius.

Of the two dialysis solutions used in equilibrium dialysis, there are two methods by which they may be introduced into the dialysis cell of the present invention. Either method can be used with the dialysis. When the sample is placed in the outer container and the dialysate is placed in the inner container the user can simply puncture the seal or open the snap-lock cap to access the dialysate.

Because the outer container of the of the invention is a substantially rigid elongate tube it may be used with automated liquid handling systems such as a automated pipettors. The design allows freedom from human intervention because the dialysis cells can be used with an automated pipettor and prepared in advance with buffer solution placed within the outer container, because they are in the general shape of a test tube and require only the insertion of a quantity of sample.

Automated liquid handling systems and more specifically automated pipettors are machines or robots that handle the movement of a probe in the Cartesian axes (X, Y, Z) over a work surface populated with tubes. The probe, sometimes called a "Z axis tool," carries one or more pipettors and may also be equipped with a gripper tool to manipulate sample containers. Automated pipetting robots move a suspended pipetting probe in X-Y-Z coordinates over a work deck and perform simple to very complicated pipetting protocols, including transferring liquids from one type of container to another. Their battery of pipettors ranges from individual needle probes to four-, eight-, 12-, up to 96-channel manifolds. Examples of such automated liquid handling systems are the Nichols CLSystem ID, by Nichols Institute Diagnostics of San Juan Capistrano, Calif.; the Biomek® 2000 automated liquid handle produced by the Beckman Coulter company; the MultiPROBE II™ made by the Packard Instrument Company, the SerialMate™ and PlateMate 96™ automated microplate pipetting systems made by the Matrix Technologies Corp. and the DPC Immulite.

When used with an automated pipettor a dialysis cell may be prepared by placing the dialysate buffer solution in the outer container, placing an empty inner container into the outer container and threadably attaching the two containers together, covering both of them with thin puncturable film. The automated pipettor is programmed to inject the inner container with sample solution by puncturing the thin film cover. The automated pipettor may be further programmed to remove an aliquot of dialysate from the outer container, usually by aspiration, after equilibrium and after removing the inner container and deliver it to a receptacle for whatever analytical method is desired.

Alternatively the sample may be placed in the outer container, and dialysate placed in the inner container by the automated pipettor.

The automated pipettor may be used for one or more of the needed steps in use of the dialysis cell, injecting one or both of the dialysate solutions, removing an aliquot of dialysate buffer solution after equilibrium has been reached from the inner container or the outer container and delivering that aliquot to the appropriate device for the chosen analysis.

The foregoing methods for use of the dialysis cell with an automated pipettor are made by way of example and not intended to be limiting.

When using dialysate buffer in the inner container it is best to maintain the container at 37 degrees Celsius so as not to disturb the equilibrium point.

FIG. 2 shows an inner container 5 designed to conform closely to outer container 1 when it is inserted therein. The inner container also has an open end 7 and a closed end 9. A second dialysis solution is shown at 27, is placed in the inner container. The wall of the inner container proximal to the closed end of the inner container has apertures 17, shown at FIG. 1, to allow fluid communication between the inner container and the outer container. The apertures of the inner container are covered with porous mesh on the inner wall 19 to provide support for a semipermeable membrane 21, which is placed over the outer wall over the apertures. The semipermeable membrane is held over the apertures by O-rings 23 at either end of the semipermeable membrane.

The semipermeable membrane is of the type well known in the art and in this embodiment would be approximately 0.05 mm thick, 18 mm long and of a width wide enough to surround the porous mesh component of the inner container.

The semipermeable membrane 21 is preferably placed over the lengthwise walls proximal to the closed end of the inner container and not the closed end itself because it would be vulnerable to puncture when the inner container is inserted in the outer container.

In the second embodiment the outer container 51 is first supplied with about 2.4 ml of the dialysate and the inner container 55 is then placed into the outer container. The outer container and the inner container are then threadably attached at their respective open ends, holding the two tubes fixedly attached tightly with respect to one another and maintaining a uniform distance of about 0.4 mm between the inner container and the outer container. About 0.2 ml of the sample is then added to the inner container.

A plunger shown as 81 in FIGS. 3 and 4 is then inserted through the opening of the open end 53 of the inner container to push the dialysis solution of the inner container up the length of the inner wall of the inner container, causing the solution in the inner container to come into greater contact with the inner wall of the inner container. If the plunger is centered when inserted into the inner container it maintains an uniform distance from the inner wall of the inner container and hence a uniform volume of dialysis solution around the plunger.

The parts of the second embodiment shown in FIG. 3 are shown assembled in FIG. 4 to form the dialysis cell 75 with the inner container 55 placed within the outer container 51 and the plunger 81 inserted into the inner container, displacing first dialysis solution 77 and second dialysis solution 79 thereby causing it to be brought into greater mutual contact with the semipermeable membrane 21. The second solution then maintains the uniform distance of about 0.4 mm between the plunger and the interior of the inner container. The central alignment of the plunger within is aided by the porous mesh 69, which holds the plunger off from the inner wall of the inner container in a uniform manner.

This apparatus results in a shorter equilibrium time because there is both a greater amount of semipermeable membrane surface area available, as well as little ambient dialysis solution within which any diffusion of an analyte would have to take place and hence less time needed for any diffusion of either of the solutions.

Further by way of example, a use of the dialysis cell of the second embodiment is given:

In measuring for the analyte Thyroxine (free T-4) separation must take place because the Thyroxine is also found bound to the T Beta Globulin (TBg-T4) in a typical sample. The semi-membrane separates the TBg-T4 complex found in the sample from the free T-4 that will cross over the semipermeable membrane into the dialysate buffer solution.

Any dialysis naturally involves some transport of water from the buffer side into the serum side because of the osmotic pressure of the serum proteins. One way to minimize water transport is to make the serum volume large and the dialysate volume relatively small. The embodiment of FIG. 5 accomplishes this by allowing for placement of the 2.4 ml of serum sample in the larger volume outer container and the 0.2 ml dialysate buffer solution in the smaller volume inner container. This effectively increases the pressure on the serum side to inhibit water transport. The plunger is then inserted into the inner container to drive the dialysate up the walls of the inner container. The dialysis cell is then placed in an incubator which holds the temperature at 37 degrees Celsius until equilibrium is reached. After removal of the inner container and the plunger the dialysate buffer solution is then sampled and that sample is subjected to automated analysis, radioimmunoassay or chemoluminescence.

The molecular (free T-4) diffusion required is also greatly reduced because the reaction takes place within a compact area. There are no large concentration gradients because there is not a large volume of solution and hence this minimizes any diffusion times.

This invention can be used in many equilibrium dialysis situations for the measurement of free or unbound hormones, drugs, neuro-peptides, electrolytes, any biologically active molecule which is bound to proteins in biologic fluids or, generally, any molecular separation where it is desired to separate dialyzable molecules (e.g., salts) from non-dialyzable ones (e.g., macromolecules, such as proteins).

Among substances that can be detected using the cell of the invention are thyroxine, triiodothyronine, testosterone, cortisol, estradiol, certain anticonvulsants such as carbamazepine, valproic acid or phenyltoin, or benzodiazepines such as Valium, Librium, and the like. Of particular interest is the determination of biological substances which are bound to substance-binding proteins.

Buffers are utilized that will maintain the pH at between 7.0 and 7.8, most preferably between 7.2 and 7.6. The buffers should generally comprise salts present at normal serum ion concentration, organic acid buffers, especially organic sulfonic acid buffers, antibiotics capable of inhibiting the growth of gram-positive cocci, gram-negative bacteria, and fungi. A neutral carrier not capable of binding the biological substance being determined, such as, for example, a non-T4 binding immunoglobulin, most preferably rabbit IgG, should also be present to prevent adsorption losses. A high molecular weight substance capable of binding to glass or generally to the cell dialysis walls, but incapable of binding to the biological substance being determined, such as, for example, gelatin, should be added so as to prevent nonspecific adsorption of the biological substance being determined to the walls of the dialysis cell.

Additional substances such as urea, hydroxy acids or amino acids, e.g., lactic acid or glutamic acid, can also be added to the buffer composition so as to more accurately mirror physiological serum profiles. Among organic buffers that can be utilized are: ACES (N-2-acetamido-2-aminoethane sulfonic acid); ADA (N-2-acetamidoaminodiacetic acid); Bicine (N,N-bis(2-hydroxyethyl(glycine)); Bis-tris-propane (1,3-bis[tris(hydroxymethyl)methylamino]propane); Diethylmalonic acid; Glycineamide (glycinamide); Glycylglycine; HEPES (N-2-hydroxyethylpiperazine-N-1-2-ethanesulfonic acid); HEPPS (N-2-hydroxyethylpiperazine-N-1-3-propanesulfonic acid); Imidiazole; MOPS (3-(N-morpholino)propanesulfonic acid); PIPES (piperazine(N-N-1-bis-2-ethanesulfonic acid)); TES (2-[tris-(hydroxymethyl)methyl]aminoethanesulfonic acid)); Tetramethylammonium hydroxide; Tricine (N-[tris(hydroxymethyl)methyl] glycine); Triethanolamine; TRIS (Tris(hydroxymethyl) aminomethane).

For this dialysis the preferred buffer will comprise potassium, calcium, magnesium and sodium ions in normal physiological concentrations of serum; chloride, phosphate and sulfate anions in normal physiological concentrations of serum; one of the aforementioned organic buffering compounds at concentrations sufficient to maintain substantial buffering capacity under the conditions desired at a range from 7.0 to 7.8, most preferably 7.2 to 7.6; an appropriate mixture of antibiotics as described previously in concentrations sufficient to substantially prevent or inhibit the growth of undesirable microorganisms; gelatin at a concentration sufficient to cover the dialysis cell wall and capable of preventing the adsorption of the biological substance being measured; and an additional neutral protein carrier such as rabbit I.G. at a concentration sufficient to prevent substantial adsorption losses of the substance being determined to walls or semipermeable membranes.

T-4 binding is pH dependent. The pH must be controlled in the range between 7.2 and 7.6. HEPES buffer has been chosen for pH control because its pKa at 37.degree. C. is 7.4. HEPES anion will displace T-4 from binding proteins if the concentration is greater than about 60 mm To control the pH of sera with acidosis and alkalosis, an effective HEPES concentration of 240 mM is needed. To achieve this total buffering capacity without exceeding the 60 mM anion concentration, a buffer volume 4 times the serum volume was designed. The HEPES buffer can then be distributed in a volume 5 times greater than the serum volume alone (serum=1; buffer=4), thereby reducing the serum concentration of HEPES anion to 48 mM and avoiding HEPES anion interference with T-4 equilibria, while maintaining the required overall buffering capacity.

To eliminate adsorption losses the dialysate buffer must contain protein. Gelatin and gammaglobulin do not bind T-4. They do interfere with the radioimmunoassay at high concentrations. In order to eliminate T-4 adsorption while maintaining gelatin and gammaglobulin concentrations below the level for interference, it was determined that neither protein alone was adequate. As a consequence, the dialysis buffer contains subthreshold concentration of both proteins in a formulation which eliminates T-4 adsorption to plastics and membranes.

In addition to the HEPES buffer, gelatin and gammaglobulins, the remaining constituents of the dialysate buffer include the non-protein constituents in serum with concentrations of 1 mM or more to provide a virtually physiologic environment for the dialysis reaction.

To eliminate the possibility of bacterial growth during the dialysis incubation, a mixture of penicillin, gentamycin, streptomycin and amphotercin B is used. The concentration of each constituent is below the threshold concentration needed to alter T-4 binding equilibrium. An optimized buffer for T-4 measurement is: NaCl: 5265 mg/l; DL-lactic acid: 1008 mg/l; L-glutamic acid: 561 mg/l; KCl: 224 mg/l; KH-2 PO-4: 180 mg/l; CaCl-2.2H-2 O: 275 mg/l; MgSO-4.7H-2 O: 246 mg/l; Urea: 300 mg/l; Gelatin: 500 mg/l; Rabbit IgG: 200 mg/l; HEPES sodium salt: 5891 mg/l; HEPES acid: 6046 mg/l; Penicillin: 100000 U/l; Streptomycin: 100 mg/l; Amphotericin: 250 ug/l; and Gentamycin: 100 mg/l. The buffer is prepared in deionized water prior to use.

The present invention may be embodied in other specific forms without departing from the spirit or essential characteristics of the invention. The present embodiments are presented merely as illustrative examples and are not restrictive, with the scope of the invention being indicated by the claims rather than by the foregoing description. All changes which come within the meaning and range of equivalency of the claims are therefore intended to be embraced therein.

What is claimed is:

1. A dialysis cell, comprising:
   a) a substantially rigid elongate outer container having an open end and a closed end,
   b) a substantially rigid elongate inner container sized to fit within the outer container, the inner container comprising a wall having an open end, a closed end and a lengthwise portion of the inner container wall incorporating a semipermeable membrane,
   c) a displacing member, for centrally displacing a volume of fluid from the bottom of the inner container along the wall of the inner container,
      wherein a first dialysis solution is placed in the outer container, a second dialysis solution is placed within the inner container sufficient to immerse a portion of the semipermeable membrane, the inner container is inserted into the outer container sufficient to immerse a portion of the semipermeable membrane in the first dialysis solution.

2. The dialysis cell of claim 1 wherein the lengthwise portion of the inner container wall that incorporates a semipermeable membrane comprises a plurality of apertures covered by a semipermeable membrane.

3. The dialysis cell of claim 2 wherein the displacing member of the inner container is comprised of a plunger sized to fit within the inner container and inserted within the inner container.

4. The dialysis cell of claim 3 wherein the open end of the outer container is attached to the open end of the inner container.

5. The dialysis cell of claim 4 wherein the open end of the outer container and the open end of the inner container are attached by threads on the open end of the outer container and complementary threads on the open end of the inner container threadably attached after the inner container is inserted into the outer container.

6. The dialysis cell of claim 4 wherein the open ends of the attached inner container and outer container are covered with a snap-lock lid.

7. The dialysis cell of claim 2 wherein the displacing member of the inner container is comprised of the wall of the inner container being centrally inverted into the inner container at the closed end.

8. The dialysis cell of claim 7 wherein the open end of the outer container is attached to the open end of the inner container.

9. The dialysis cell of claim 8 wherein the open end of the outer container and the open end of the inner container are attached by threads on the open end of the outer container and complementary threads on the open end of the inner container, threadably attached after the inner container is inserted into the outer container.

10. The dialysis cell of claim 8 wherein the open end of the outer container and the open end of the inner container are attached by threadably attaching a cap to the threads on the open end of the outer container after the inner container is inserted into the outer container.

11. The dialysis cell of claim 10 wherein the central portion of the cap is made of a thin film.

12. The dialysis cell of claim 8 wherein the open end of the outer container and the open end of the inner container are attached by joining a snap-lock flange on the open end of the outer container and a complementary snap-lock flange on the open end of the inner container, that are joined after the inner container is inserted into the outer container.

13. The dialysis cell of claim 1 wherein the semipermeable membrane that is incorporated into the lengthwise portion of the inner container wall comprises a plurality of apertures covered by porous mesh and a semipermeable membrane.

14. The dialysis cell of claim 13 wherein the displacing member of the inner container is comprised of the wall of the inner container being centrally inverted into the inner container at the closed end.

15. The dialysis cell of claim 14 wherein the open end of the outer container is attached to the open end of the container.

16. The dialysis cell of claim 15 wherein the open end of the outer container and the open end of the inner container are attached by threads on the open end of the outer container and complementary threads on the open end of the inner container, threadably attached after the inner container is inserted into the outer container.

17. The dialysis cell of claim 15 wherein the open end of the outer container and the open end of the inner container are attached by threadably attaching a cap to the threads on the open end of the outer container after the inner container is inserted into the outer container.

18. The dialysis cell of claim 15 wherein the central portion of the cap is made of a thin film.

19. The dialysis cell of claim 15 wherein the open end of the outer container and the open end of the inner container are attached by joining a snap-lock flange on the open end of the outer container and a complementary snap-lock flange on the open end of the inner container, that are joined after the inner container is inserted into the outer container.

20. The dialysis cell of claim 13 further wherein the displacing member of the inner container is comprised of a plunger sized to fit within the inner container and inserted within the inner container.

21. The dialysis cell of claim 20 wherein the open end of the outer container is attached to the open end of the inner container.

22. The dialysis cell of claim 21 wherein the open end of the outer container and the open end of the inner container are attached by threads on the open end of the outer container and complementary threads on the open end of the inner container threadably attached after the inner container is inserted into the outer container.

23. The dialysis cell of claim 21 wherein the open ends of the attached inner container and outer container are covered with a snap-lock lid.

24. The dialysis cell of claim 21 wherein the open end of the outer container and the open end of the inner container are attached by threads on the open end of the outer container joined to complementary threads on the open end of the inner container threadably attached after the inner container is inserted into the outer container.

25. A dialysis cell, comprising:
   a) a substantially rigid elongate outer container having an open end and a closed end,
   b) a substantially rigid elongate inner container sized to fit within the outer container, the inner container comprising a wall having an open end, a closed end and a lengthwise portion of the inner container wall incorporating a semipermeable membrane,
   c) a displacing member, centrally displacing the volume of the inner container,
      wherein a first dialysis solution is placed in the outer container, a second dialysis solution is placed within the inner container sufficient to immerse a portion of the semipermeable membrane, the inner container is inserted into the outer container sufficient to immerse a portion of the semipermeable membrane in the first dialysis solution,
      wherein the lengthwise portion of the inner container wall that incorporates a semipermeable membrane comprises at least one aperture covered by a semipermeable membrane,
      wherein the displacing member of the inner container is comprised of the wall of the inner container being centrally inverted into the inner container at the closed end,
      wherein the open ends of the outer container is attached to the open end of the inner container, and
      wherein the open ends of the attached inner container and outer container are both covered with a thin puncturable film.

26. A dialysis cell, comprising:
   a) a substantially rigid elongate outer container having an open end and a closed end,
   b) a substantially rigid elongate inner container sized to fit within the outer container, the inner container comprising a wall having an open end, a closed end and a lengthwise portion of the inner container wall incorporating a semipermeable membrane,
   c) a displacing member, centrally displacing the volume of the inner container,
      wherein a first dialysis solution is placed in the outer container, a second dialysis solution is placed within the inner container sufficient to immerse a portion of the semipermeable membrane, the inner container is inserted into the outer container sufficient to immerse a portion of the semipermeable membrane in the first dialysis solution,
      wherein the lengthwise portion of the inner container wall that incorporates a semipermeable membrane comprises at least one aperture covered by a semipermeable membrane,
      wherein the displacing member of the inner container is comprised of a plunger sized to fit within the inner container and inserted within the inner container,
      wherein the open end of the outer container is attached to the open end of the inner container, and
      wherein the open ends of the attached inner container and outer container are both covered with a thin puncturable film.

27. A dialysis cell, comprising:
   a) a substantially rigid elongate outer container having an open end and a closed end,
   b) a substantially rigid elongate inner container sized to fit within the outer container, the inner container comprising a wall having an open end, a closed end and a lengthwise portion of the inner container wall incorporating a semipermeable membrane,
   c) a displacing member, centrally displacing the volume of the inner container,
      wherein a first dialysis solution is placed in the outer container, a second dialysis solution is placed within the inner container sufficient to immerse a portion of the semipermeable membrane, the inner container is inserted into the outer container sufficient to immerse a portion of the semipermeable membrane in the first dialysis solution,
      wherein the semipermeable membrane that is incorporated into the lengthwise portion of the inner container wall comprises at least one aperture covered by porous mesh and a semipermeable membrane,
      wherein the displacing member of the inner container is comprised of the wall of the inner container being centrally inverted into the inner container at the closed end,
      wherein the open end of the outer container is attached to the open end of the inner container, and
      wherein the open ends of the attached inner container and the outer container are both covered with a thin puncturable film.

28. A dialysis cell, comprising:
   a) a substantially rigid elongate outer container having an open end and a closed end,
   b) a substantially rigid elongate inner container sized to fit within the outer container, the inner container comprising a wall having an open end, a closed end and a lengthwise portion of the inner container wall incorporating a semipermeable membrane,
   c) a displacing member, centrally displacing the volume of the inner container,
      wherein a first dialysis solution is placed in the outer container, a second dialysis solution is placed within the inner container sufficient to immerse a portion of the semipermeable membrane, the inner container is inserted into the outer container sufficient to immerse a portion of the semipermeable membrane in the first dialysis solution,
      wherein the semipermeable membrane that is incorporated into the lengthwise portion of the inner container wall comprises at least one aperture covered by porous mesh and a semipermeable membrane,
      wherein the displacing member of the inner container is comprised of a plunger sized to fit within the inner container and inserted within the inner container,
      wherein the open end of the outer container is attached to the open end of the inner container, and
      wherein the open ends of the attached inner container and outer container are both covered with a thin puncturable film.

29. A dialysis cell, comprising:
   a) a substantially rigid elongate outer container having an open end and a closed end,
   b) a substantially rigid elongate inner container sized to fit within the outer container, the inner container comprising a wall having an open end, a closed end and a lengthwise portion of the inner container wall incorporating a semipermeable membrane,
   c) a displacing member, for centrally displacing a volume of fluid from the bottom of the inner container along the wall of the inner container,
      wherein a first dialysis solution is placed in the outer container, a second dialysis solution is placed within the inner container sufficient to immerse a portion of the semipermeable membrane, the inner container is inserted into the outer container sufficient to immerse a portion of the semipermeable membrane in the first dialysis solution, and wherein the open ends of the attached inner container and outer container are both covered with a thin puncturable film.

* * * * *